(12) United States Patent
Ghosh et al.

(10) Patent No.: US 12,263,188 B2
(45) Date of Patent: Apr. 1, 2025

(54) METHODS AND COMPOSITIONS FOR TREATING STROKE

(71) Applicant: Revalesio Corporation, Tacoma, WA (US)

(72) Inventors: Supurna Ghosh, Tacoma, WA (US); Helmut Andreas Kalmes, Tacoma, WA (US)

(73) Assignee: Revalesio Corporation, Tacoma, WA (US)

( * ) Notice: Subject to any disclaimer, the term of this patent is extended or adjusted under 35 U.S.C. 154(b) by 769 days.

(21) Appl. No.: 17/187,437

(22) Filed: Feb. 26, 2021

(65) Prior Publication Data

US 2021/0177891 A1 Jun. 17, 2021

Related U.S. Application Data

(63) Continuation of application No. PCT/US2019/049196, filed on Aug. 30, 2019.

(60) Provisional application No. 62/726,166, filed on Aug. 31, 2018.

(51) Int. Cl.
| | |
|---|---|
| *A61K 33/00* | (2006.01) |
| *A61K 9/00* | (2006.01) |
| *A61K 47/02* | (2006.01) |
| *A61P 9/10* | (2006.01) |

(52) U.S. Cl.
CPC ............ *A61K 33/00* (2013.01); *A61K 9/0019* (2013.01); *A61K 47/02* (2013.01); *A61P 9/10* (2018.01)

(58) Field of Classification Search
CPC ...... A61K 33/00; A61K 9/0019; A61K 47/02; A61K 9/0085; A61K 9/08; A61K 41/00; A61P 9/10; A61M 2202/0476; A61M 2210/0693; A61M 2202/0007
USPC .......................................................... 424/489
See application file for complete search history.

(56) References Cited

U.S. PATENT DOCUMENTS

| | | | |
|---|---|---|---|
| 4,445,888 A | 5/1984 | Osterholm | |
| 4,830,849 A * | 5/1989 | Osterholm | ............. A61K 31/02 |
| | | | 436/127 |
| 5,084,011 A | 1/1992 | Grady | |
| 10,125,359 B2 | 11/2018 | Watson et al. | |
| 2008/0281001 A1 | 11/2008 | Wood et al. | |
| 2010/0015235 A1 | 1/2010 | Watson et al. | |

(Continued)

FOREIGN PATENT DOCUMENTS

| | | |
|---|---|---|
| CA | 3084634 A1 | 9/2012 |
| CN | 106539819 A | 3/2017 |

(Continued)

OTHER PUBLICATIONS

"Dementia in ALS" Webmed, 2019, pp. 1-10.

(Continued)

*Primary Examiner* — Isaac Shomer
*Assistant Examiner* — Bryan James Rego
(74) *Attorney, Agent, or Firm* — KNOBBE, MARTENS, OLSON & BEAR LLP

(57) ABSTRACT

Some embodiments include methods of treating, inhibiting, or ameliorating ischemic stroke or a symptom thereof in a subject. Some embodiments include oxygenated fluid for use in treating, inhibiting, or ameliorating ischemic stroke. The oxygenated fluid may comprise charge-stabilized oxygen-containing nanostructures.

17 Claims, 6 Drawing Sheets

(56) References Cited

U.S. PATENT DOCUMENTS

| | | | |
|---|---|---|---|
| 2010/0028441 A1* | 2/2010 | Watson | A61P 25/00 977/773 |
| 2010/0098659 A1 | 4/2010 | Watson et al. | |
| 2010/0310609 A1 | 12/2010 | Watson et al. | |
| 2012/0263764 A1 | 10/2012 | Watson | |
| 2014/0329869 A1 | 11/2014 | Bozic et al. | |
| 2015/0320705 A1 | 11/2015 | Matsuda et al. | |
| 2016/0041122 A1 | 2/2016 | German et al. | |
| 2018/0214303 A1* | 8/2018 | Dabrowiak | A61F 7/0085 |
| 2019/0298653 A1 | 10/2019 | Yamanouchi et al. | |
| 2020/0061103 A1 | 2/2020 | Kalmes et al. | |

FOREIGN PATENT DOCUMENTS

| | | |
|---|---|---|
| JP | 2011/001271 A | 8/2012 |
| WO | WO 2006/050451 A2 | 5/2006 |
| WO | WO 2009/134728 A2 | 11/2009 |
| WO | WO 2012/121403 A1 | 9/2012 |
| WO | WO 2017/172893 A1 | 10/2017 |
| WO | WO 2017/195852 A1 | 11/2017 |
| WO | WO 2019/226926 A1 | 11/2019 |
| WO | WO 2020/047497 A1 | 3/2020 |

OTHER PUBLICATIONS

Beghi et al., Randomized double-blind placebo-controlled trial of acetyl-L-carnitine for ALS, *Amyotrophic Lateral Sclerosis and Frontotemporal Degeneration*, 2013.
Berry et al., NurOwn, phase 2, randomized, clinical trial in patients with ALS, *Neurology*, pp. e2294-e2305, vol. 93, No. 24, Dec. 10, 2019.
Czaplinski et al. "Forced vital capacity (FVC) as an indicator of survivor and disease progression in an ALS clinic population" J. Neurol. Neurosurg. Psychiatry (2006) 77, pp. 390-392.
De la Rubia et al., Efficacy and tolerability of EH301 for amyotrophic lateral sclerosis: a randomized, double-blind, placebo-controlled human pilot study, *Amyotrophic Lateral Sclerosis and Frontotemporal Degeneration*, 2019.
Ella et al., Tauroursodeoxycholic acid in the treatment of patients with amyotrophic lateral sclerosis, *European Journal of Neurology*, 23: 45-52, 2016.
File History of U.S. Appl. No. 12/772,028, filed Apr. 30, 2010.
File History of U.S. Appl. No. 14/885,935, filed Oct. 16, 2015.
Mario Negri Institute for Pharmacological Research. "The Effect of RNS60 on ALS Biomarkers (RNS60)" ClinicalTrials.gov. Retrieved from < https://clinicaltrials.gov/ct2/show/NCT03456882> on May 13, 2021. pp. 1-9.
Mondal et al. "Protection of Tregs, Suppression of Th1 and Th17 Cells, and Amelioration of Experimental Allergic Encephalomyelitis by a Physically-Modified Saline" PLOS One 7(12):e51869. pp. 1-18.
Mora et al., Masitinib as an add-on therapy to riluzole in patients with amyotrophic lateral sclerosis: a randomized clinical trial, *Amyotrophic Lateral Sclerosis and Frontotemporal Degeneration*, 21: 5-14, 2020.

Oh et al., Repeated Intrathecal Mesenchymal Stem Cells for Amyotrophic Lateral Sclerosis, *Ann Neurol*, 84:361-373, 2018.
Paganoni S. "A Pilot Study of RNS60 in Amyotrophic Lateral Sclerosis (ALS)" ClinicalTrials.gov. Retrieved from <https://clinicaltrials.gov/ct2/show/NCT02525471> on May 13, 2021. pp. 1-9.
Revalesio Corporation. "Nebulized RNS60 for the Treatment of Amyotrophic Lateral Sclerosis" ClinicalTrials.gov. Retrieved from < https://www.clinicaltrials.gov/ct2/show/NCT02988297> on May 13, 2021. pp. 1-7.
Shefner et al., A phase III trial of tirasemtiv as a potential treatment for amyotrophic lateral sclerosis, *Amyotrophic Lateral Sclerosis and Frontotemporal Degeneration*, 20: 584-594, 2019.
Shefner et al., A randomized, placebo-controlled, double-blind phase IIb trial evaluating the safety and efficacy of tirasemtiv in patients with amyotrophic lateral sclerosis, *Amyotrophic Lateral Sclerosis and Frontotemporal Degeneration*, 2016.
Singhal, "A review of oxygen therapy in ischemic stroke", Neurological Research, vol. 29 Mar. 2007.
The Writing Group on behalf of the Edaravone (MCI-186) ALS 19 Study Group, Safety and efficacy of edaravone in well defined patients with amyotrophic lateral sclerosis: a randomised, double-blind, placebo-controlled trial, *Lancet Neurol*, http://dx.doi.org/10.1016/S1474-4422(17)30115-1, 2017.
Vallarola et al. "RNS60 exerts therapeutic effects in the SOD1 ALS mouse model through protective glia and peripheral nerve rescue" J. Neuroinflammation (2018) 15:65, pp. 1-22.
International Search Report and Written Opinion mailed Aug. 15, 2019 in International Application No. PCT/US2019/033808, in 11 pages.
International Search Report and Written Opinion mailed Nov. 13, 2019 in International Application No. PCT/US2019/049196, in 7 pages.
Non-final office action dated Jul. 10, 2023 issued in corresponding Japanese patent application No. 2021-510642.
Kalmes et al., "Acute Coronary Syndromes—A Saline-Based Therapeutic Containing Charge—Stabilized Nanostructures Protects against Cardiac Ischemia/Reperfusion Injury", E106, JACC, Mar. 12, 2013, p. E106, XP055917704 (retrieved on May 3, 2022).
Khasnavis et al., "Suppression of Nuclear Factor-B Activation and Inflammation in Microglia by Physically Modified Saline", Journal of Biological Chemistry, vol. 287, No. 35, Aug. 24, 2012, pp. 29529-29542, XP055062907, ISSN: 0021-9258, DOI: 10.1074/jbc.M111.338012.
Extended European Search Report mailed on May 17, 2022, in European Application No. EP 19855658.1, in 12 pages.
Revalesio, Feb. 7, 2024, Revalesio Announces Positivetopline Data From Phase 2 Rescue Study of RNS60 Inpatients With Acute Ischemicstroke in Late-Breaking Oralpresentation at ISC 2024 [Press release].
Office Action issued in corresponding Australian application No. 2019331902, dated May 21, 2024.
Notice of Allowance issued in Japanese Application No. 2021-510642, dated Apr. 8, 2024.
Office Action issued in corresponding Korean application No. 10-2021-7009632, dated Jan. 16, 2025.

\* cited by examiner

METHODS AND COMPOSITIONS FOR TREATING STROKE

CROSS-REFERENCE TO RELATED APPLICATIONS

The present application is a 35 U.S.C. 111(a) Continuation Application of International Application No. PCT/US2019/049196, filed Aug. 30, 2019, designating the United States of America and published in the English language, which claims the benefit of U.S. Provisional Application No. 62/726,166, filed Aug. 31, 2018, each of which is incorporated by reference in its entirety herein.

BACKGROUND

Stroke is a medical condition characterized by insufficient blood flow to the brain, which can result in damage to brain tissues, including cell death. Generally, stroke falls into the categories of ischemic stroke, attributable to blockade of blood flow in an artery to the brain caused by a thrombus or an embolus, and hemorrhagic stroke, attributable to bleeding from a blood vessel in the brain. Stroke is a leading cause of disability and death in adults. More than 795,000 cases of strokes, 87% of which are ischemic strokes, occur in the United States every year, with many more cases worldwide (Benjamin et al., "Heart Disease and Stroke Statistics-2017 Update: A Report From the American Heart Association" Circulation 135(10):e146-e603, 2017).

FIELD

Embodiments herein relate to methods and compositions for use in treating, inhibiting, and/or ameliorating stroke or one or more symptoms thereof.

SUMMARY

In some embodiments, a method of treating, inhibiting, or ameliorating stroke, such as ischemic stroke or a symptom thereof in a subject is provided. The method can comprise administering an oxygenated fluid to the subject. The administering can occur at or immediately following the onset of ischemic stroke symptoms in the subject, for example, within 24 hours after the onset of ischemic stroke symptoms in the subject, such as within 1, 3, 6, 12, 18, or 24 hours. By way of example, the oxygenated fluid can comprise or consist essentially of dissolved oxygen. For example, at least 50%, 60%, 70%, 80%, or 90% of the oxygen in the oxygenated fluid can be dissolved oxygen. In some embodiments, the oxygenated fluid is oxygenated by dissolved oxygen. In some embodiments, at least 50%, 60%, 70%, 80%, or 90% of the oxygenation in the oxygenated fluid comprises dissolved oxygen. By way of example, the oxygenated fluid can comprise charge-stabilized oxygen, such as charge-stabilized oxygen-containing nanostructures. In some embodiments, the oxygenated fluid is a pharmaceutical saline solution comprising charge-stabilized oxygen-containing nanostructures, a majority of the nanostructures having a diameter of less than 100 nanometers, in which the pharmaceutical saline solution comprised at least 20 ppm oxygen at the time it was manufactured. In some embodiments, the administering comprises delivering the oxygen of the oxygenated fluid (e.g. oxygen of oxygen-containing nanostructures) to hypoxic brain cells of the subject. In some embodiments, the administering comprises delivering the oxygen of the oxygenated fluid to brain cells of the subject, in which said brain cells were subjected to ischemia followed by reperfusion. In some embodiments, the brain cells are selected from the group consisting of neurons, glial cells, oligodendrocytes, and microglia. In some embodiments, the administered oxygenated fluid is effective to inhibit hypoxia of brain cells of the subject. In some embodiments, the administered oxygenated fluid is effective to inhibit reperfusion damage to brain cells of the subject. In some embodiments, the administered oxygenated fluid is effective to inhibit a decline in a behavior following the stroke, for example one or more of consciousness, defense reaction, grasp reflex, extremity movement, gait, circling, bradykinesia, balance, neglect, visual field cut/hemianopsia or facial weakness. In some embodiments, the brain cells are selected from the group consisting of neurons, glial cells, oligodendrocytes, and microglia. In some embodiments, the oxygenated fluid is administered in a dose of at least 2 cc/kg. In some embodiments, the oxygenated fluid is administered in a dose of at least 20 cc/kg. In some embodiments, the oxygenated fluid is administered at about 0.1-20 cc/kg/h. In some embodiments, the oxygenated fluid is administered at about 1-7 cc/kg/h. In some embodiments, the oxygenated fluid is administered for at least about 1, 2, 3, 4, 5, 6, 7, 8, 9, or 10 hours. In some embodiments, the administering is a first line treatment for ischemic stroke. In some embodiments, the administering is within six hours after the commencement of the ischemic stroke. In some embodiments, the administering is within three hours after the commencement of the ischemic stroke. In some embodiments, the administering is three to six hours after the commencement of the ischemic stroke. In some embodiments, the administering is 1 to 24 hours, 1 to 18 hours, 1 to 12 hours, 1 to 6 hours, 1 to 3 hours, 3 to 24 hours, 3 to 12 hours, 3 to 6 hours, 6 to 24 hours, 6 to 18 hours, 6 to 12 hours, 12 to 24 hours, 12 to 18 hours, or 18 to 24 hours after the onset of ischemic stroke symptoms. In some embodiments, the administering is intravenous. In some embodiments, the administering does not comprise inhalation. In some embodiments, the oxygenated fluid comprises at least 40 ppm oxygen at standard temperature and pressure. In some embodiments, the oxygenated fluid comprises saline. In some embodiments, the oxygenated fluid comprises saline for injection. In some embodiments, the oxygenated fluid is sterile (for example, immediately prior to administering, noting that such a fluid is not expected to be sterile after it is administered to the subject). In some embodiments, the oxygenated fluid is part of, or is a pharmaceutical composition. In some embodiments, the oxygenated fluid does not comprise blood. In some embodiments, the oxygenated fluid does not comprise perfluorocarbon. In some embodiments, the oxygenated fluid is oxygenated by dissolved oxygen. In some embodiments, at least 50%, 60%, 70%, 80%, or 90% of the oxygenation in the oxygenated fluid comprises dissolved oxygen. In some embodiments, the oxygen in the oxygenated fluid comprises modified or charged oxygen species. In some embodiments, the oxygenated fluid comprises no more than trace amounts of ozone. In some embodiments, the oxygen in the oxygenated fluid has been present in an amount of at least 15 ppm at standard temperature and pressure for at least 3 hours. In some embodiments, the oxygen in the oxygenated fluid has been present in an amount of at least 40 ppm at standard temperature and pressure for at least 3 hours. In some embodiments, the nanostructures comprise nanobubbles, a majority of the nanobubbles having a diameter of less than 100 nanometers. In some embodiments, the method further comprises administering an additional therapeutic agent to the subject. In some embodiments, the method further comprises performing a thrombectomy and/or embolectomy on the subject.

Some embodiments include an oxygenated fluid as described herein for use in treating, inhibiting, or ameliorating a symptom of ischemic stroke, the use comprising any method described herein. By way of example, the oxygenated fluid may comprise charge-stabilized oxygen-containing nanostructures as described herein.

DETAILED DESCRIPTION

Figure 2A:
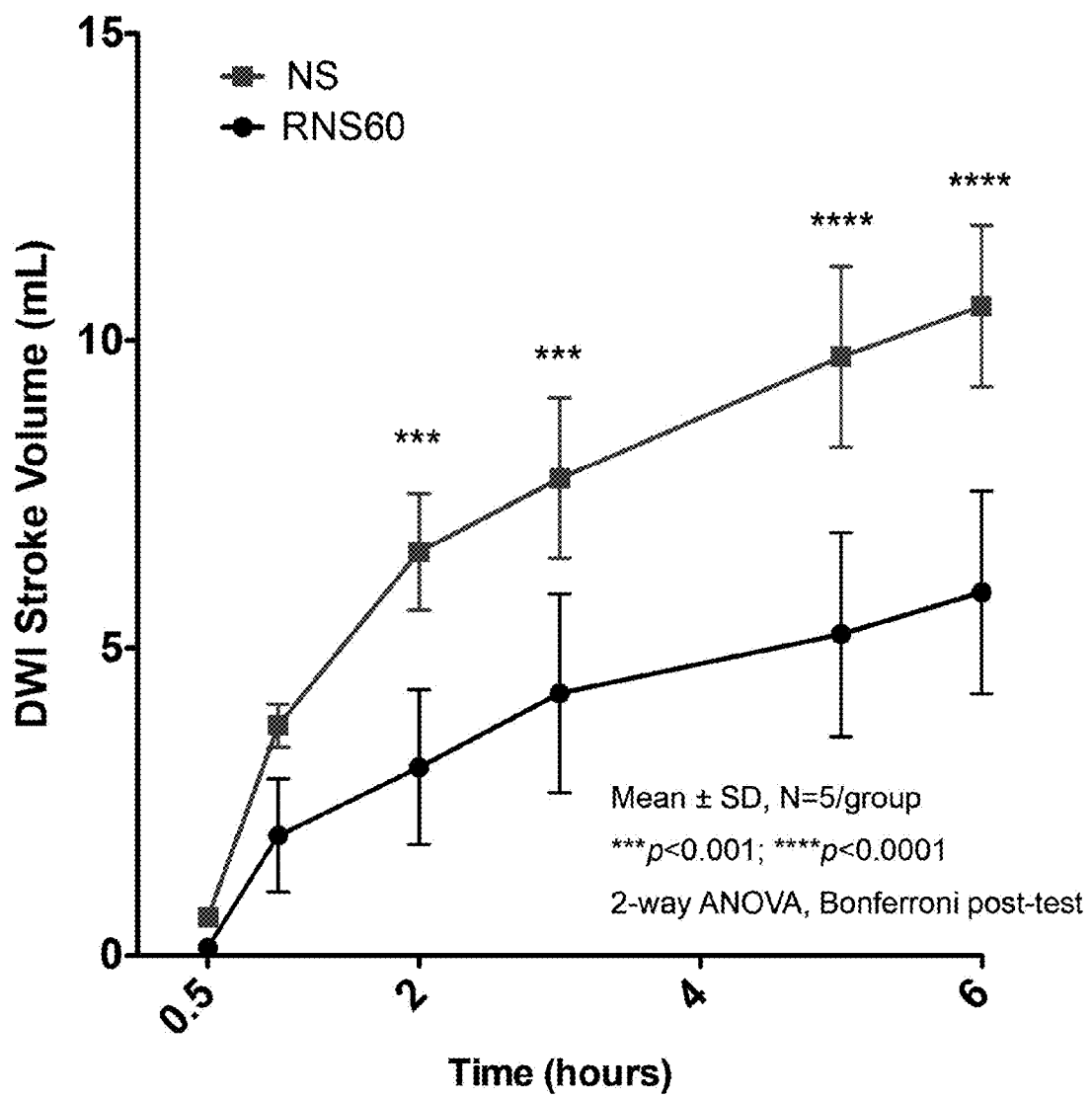
FIGS. 2A-B are a series of graphs showing the effects of administering a fluid comprising charge-stabilized oxygen-containing nanostructures of some embodiments in a primate model of ischemic stroke. Shown are the infarct volume measured by magnetic resonance Diffusion Weighted Imaging (DWI) (FIG. 2A), and the volume of salvageable brain tissue (ischemic penumbra), which was calculated as the difference between the DWI volume and the area at risk measured by Perfusion Weighted Imaging (PWI) at baseline (FIG. 2B) for primates that underwent mid cerebral artery occlusion and were treated with an oxygenated fluid according to some embodiments ("RNS60") and normal-saline treated controls ("NS").
Figure 2B:
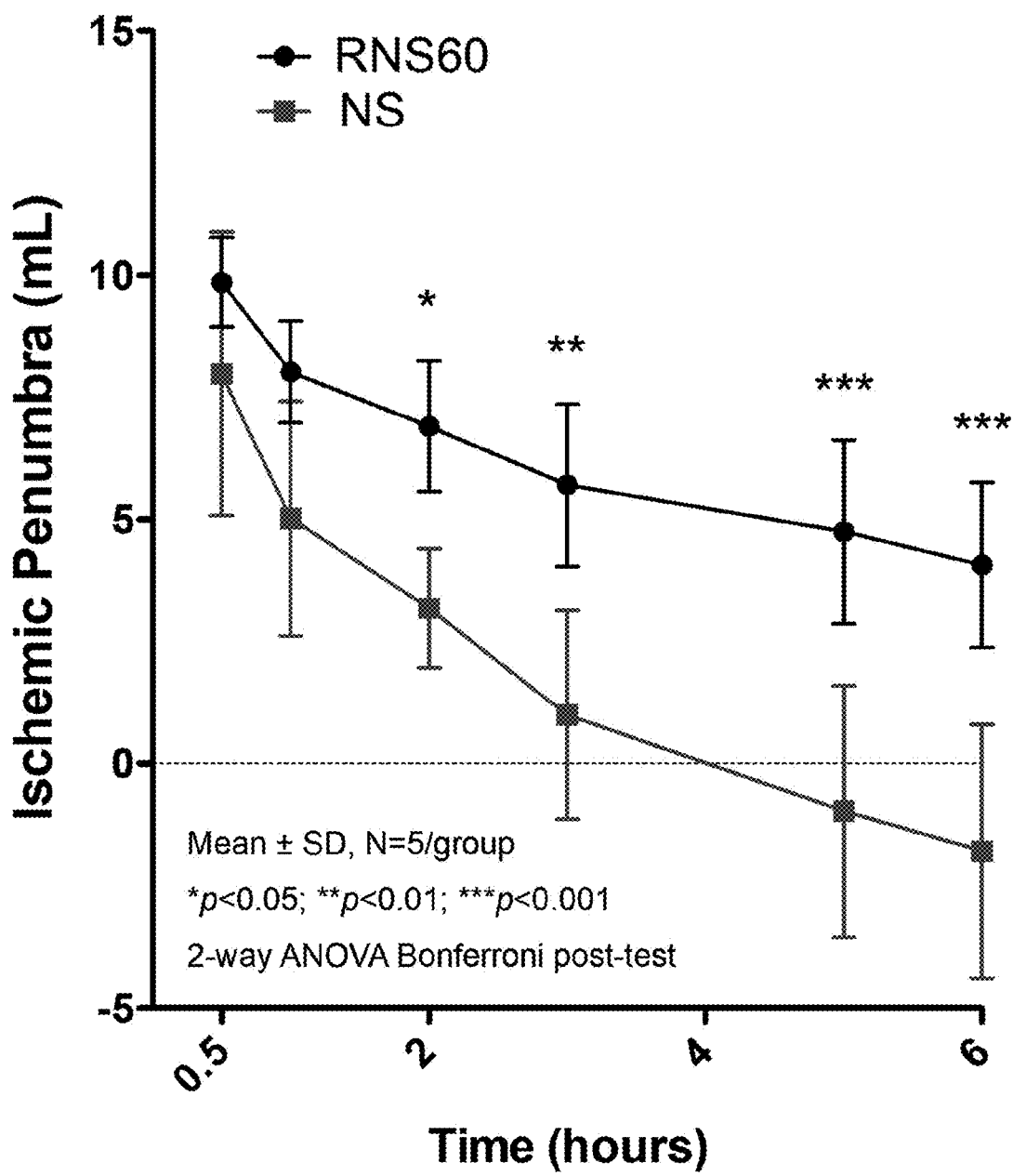

Some embodiments relate to oxygenated fluids for use in treating, inhibiting, or ameliorating ischemic stroke or a symptom thereof. For example, the oxygenated fluids can comprise charge-stabilized oxygen-containing nanostructures. It is shown herein that administering an oxygenated fluid after the onset of ischemic stroke achieves significant reduction in brain lesion size compared to saline-treated controls (Example 2). Moreover, the inhibition of brain lesions is maintained in the hours after the stroke (FIGS. 2A-B). Conventionally, endeavors to administer oxygen gas have been subject to concerns about risks of increased oxygen stress and oxygen toxicity, for example from free radicals. Without being limited by theory, it is contemplated that oxygenated fluids as described herein (for example, oxygenated fluids comprising dissolved oxygen such as oxygenated fluids comprising charge-stabilized oxygen such as charge-stabilized oxygen-containing nanostructures) can provide neuroprotective effects, for example, by delivering oxygen to hypoxic brain cells and/or brain cells that were subjected to ischemia followed by reperfusion. Examples of brain cells include neurons, glial cells (such as oligodendrocytes and/or microglia), or a combination of two or more of the listed cell types. In some embodiments, the oxygenated fluid comprises, consists essentially of, or consists of a saline solution comprising at least 40 ppm oxygen. In some embodiments, the oxygenated fluid is a pharmaceutical solution, for example comprising saline for injection. A method of treating, inhibiting, or ameliorating ischemic stroke or a symptom thereof of some embodiments can comprise administering an effective amount of the oxygenated fluid to a subject at or immediately following the onset of stroke symptoms. As used herein in "immediately following the onset of stroke symptoms" (and variations of this root term) has its ordinary and customary meaning as would be understood by one of ordinary skill in the art in view of this disclosure. It refers to an initial time period after the onset of stroke symptoms during which first line therapies can be administered, for example, within 24 hours, 18 hours, 12 hours, 6 hours, 3 hours, or 1 hour after the onset of the stroke symptoms, including ranges between any two of the listed values, for example 1 to 24 hours, 1 to 18 hours, 1 to 12 hours, 1 to 6 hours, 3 to 24 hours, 3 to 18 hours, 3 to 12 hours, 3 to 6 hours, 6 to 24 hours, 6 to 18 hours, 6 to 12 hours, 12 to 24 hours, 12 to 18 hours, or 18 to 24 hours after the onset of stroke symptoms.

Oxygenated Fluids

An "oxygenated fluid" as used herein, has its ordinary and customary meaning as would be understood by one of ordinary skill in the art in view of this disclosure. It can refer to a fluid comprising greater amounts of dissolved oxygen than oxygen in equilibrium with the ambient air. For example, an oxygenated fluid as described herein may comprise at least 15 ppm oxygen at standard temperature and pressure, such as at least 20 ppm, 25 ppm, 30 ppm, 35 ppm, 40 ppm, 45 ppm, 50 ppm, 55 ppm, 60 ppm, 65 ppm, 70 ppm, 75 ppm, or 80 ppm oxygen, including ranges between any two of the listed values, for example 15 ppm-80 ppm, 20 ppm-80 ppm, 25 ppm-80 ppm, 30 ppm-80 ppm, 35 ppm-80 ppm, 40 ppm-80 ppm, 45 ppm-80 ppm, 50 ppm-80 ppm, 55 ppm-80 ppm, 60 ppm-80 ppm, 15 ppm-75 ppm, 20 ppm-75 ppm, 25 ppm-75 ppm, 30 ppm-75 ppm, 35 ppm-75 ppm, 40 ppm-75 ppm, 45 ppm-75 ppm, 50 ppm-75 ppm, 55 ppm-75 ppm, 60 ppm-75 ppm, 15 ppm-70 ppm, 20 ppm-70 ppm, 25 ppm-70 ppm, 30 ppm-70 ppm, 35 ppm-70 ppm, 40 ppm-70 ppm, 45 ppm-70 ppm, 50 ppm-70 ppm, 55 ppm-70 ppm, 60 ppm-70 ppm, 15 ppm-65 ppm, 20 ppm-65 ppm, 25 ppm-65 ppm, 30 ppm-65 ppm, 35 ppm-65 ppm, 40 ppm-65 ppm, 45 ppm-65 ppm, 50 ppm-65 ppm, 55 ppm-65 ppm, 60 ppm-65 ppm, 15 ppm-60 ppm, 20 ppm-60 ppm, 25 ppm-60 ppm, 30 ppm-60 ppm, 35 ppm-60 ppm, 40 ppm-60 ppm, 45 ppm-60 ppm, 50 ppm-60 ppm, or 55 ppm-60 ppm of dissolved oxygen. It will be understood that an "oxygenated fluid" as described herein refers to a solution containing oxygen in addition to the solute of the solution, and thus refers to the structure of the solution. Unless explicitly stated otherwise, "oxygenated fluid" as used herein does not imply any particular method of making the oxygenated fluid. In some embodiments, the oxygenated fluid is oxygenated with dissolved oxygen. For example, at least 50%, 60%, 70%, 80%, or 90% of the oxygenation in the oxygenated fluid can comprise dissolved oxygen. In some embodiments, the oxygenated fluid comprises or consists essentially of dissolved oxygen. In some embodiments, at least 50%, 60%, 70%, 80%, or 90% of the oxygen in the oxygenated fluid is dissolved oxygen. In some embodiments, the oxygenated fluid does not comprise perfluorocarbon. In some embodiments, the oxygenated fluid comprises charged-stabilized oxygen. In some embodiments, the oxygenated fluid comprises charged-stabilized oxygen-containing nanostructures.

A "fluid comprising charge-stabilized oxygen-containing nanostructures" as used herein, has its ordinary and customary meaning as would be understood by one of ordinary skill in the art in view of this disclosure. It can refer to electrokinetically-generated fluids comprising oxygen and ions. It will be understood that wherever "electrokinetically-generated fluids" (including variations of this root term) are mentioned herein, fluids comprising charge-stabilized oxygen-containing nano structures are also expressly contemplated. The oxygen containing nanostructures can have an average diameter of less than about 100 nanometers. It will be appreciated that a "fluid comprising charge-stabilized oxygen-containing nanostructures" is a type of oxygenated fluid and is suitable wherever an "oxygenated fluid" is mentioned herein. In some embodiments, the oxygenated fluid comprising charge-stabilized oxygen-containing nanostructures comprises, consists essentially of, or consists of an ionic aqueous solution of charge-stabilized oxygen-containing nanostructures (such as nanobubbles), in which the majority of the nanostructures have an average diameter of less than about 100 nanometers and are stable in the ionic aqueous solution. The oxygenated fluids comprising charge-stabilized oxygen-containing nanostructures are distinct from other oxygenated fluids, for example, oxygenated non-electrokinetic fluids (e.g., pressure pot oxygenated fluids and the like). In methods, uses, and compositions of some embodiments, the oxygenated fluid comprising charge-stabilized oxygen-containing nanostructures comprises, consists essentially of, or consists of a pharmaceutical saline solution comprising stabilized oxygen-containing nanobubbles, a majority of the nanobubbles having a diameter of less than 100 nanometers. The pharmaceutical saline solution can comprise greater than or equal to 40 ppm oxygen. In some embodiments, for the oxygenated fluid comprising charge-stabilized oxygen-containing nanostructures of any of the methods, uses, or medicaments herein, oxygen in the oxygenated fluid comprising charge-stabilized oxygen-containing nanostructures has been present in an amount of at least 40 ppm at standard temperature and pressure (0° C. and 100 kPa) for at least 3 hours. In methods, uses, or medicaments of some embodiments herein, the pharmaceutical saline solution comprised greater than or equal to 50 ppm oxygen at the time that the pharmaceutical saline solution was manufactured. In some embodiments, the oxygenated fluid comprises, consists essentially of, or consists of RNS60.

Oxygenated fluids, including fluids comprising charge-stabilized oxygen-containing nanostructures suitable for methods, medicaments, and uses of some embodiments herein can be produced, for example, using the Mixing Device described in detail in U.S. Pat. No. 9,745,567, which is herein incorporated by reference in its entirety. Methods and devices for making oxygenated fluids, such as fluids comprising charge-stabilized oxygen-containing nanostructures are also described in detail in US Pub. No. 2008/02190088 and International Application No. WO2008/052143, each of which is herein incorporated by reference in its entirety. By way of example, suitable oxygenated fluids (such as fluids comprising charge-stabilized oxygen-containing nanostructures) for methods, medicaments, and uses of some embodiments herein can be generated in the presence of hydrodynamically-induced, localized (e.g., non-uniform with respect to the overall fluid volume) electrokinetic effects (e.g., voltage/current pulses), such as device feature-localized effects. In some embodiments, the oxygenated fluid comprising charge-stabilized oxygen-containing nanostructures is characterized by hydrodynamically-induced, localized electrokinetic effects in combination with surface-related double layer and/or streaming current effects.

The oxygenated fluid of methods, uses, and medicaments of some embodiments comprises charge-stabilized oxygen-containing nanostructures. In some embodiments, the oxygenated fluid (e.g., an oxygenated fluid comprising charge-stabilized oxygen-containing nanostructures) is superoxygenated, for example comprising 20 ppm, 40 ppm, or 60 ppm dissolved oxygen, including ranges between any two of the listed values. It has been shown, for example, that oxygenated fluids comprising charge-stabilized oxygen-containing nanostructures having dissolved oxygen levels of 15 ppm or less can have physiological effects that are qualitatively similar to fluids comprising charge-stabilized oxygen-containing nanostructures having higher dissolved oxygen levels (See U.S. Pat. No. 9,745,567 at Examples 16 and 24), and thus it is contemplated that oxygenated fluids comprising about 15 ppm oxygen or more in accordance with embodiments herein can have physiological effects. Accordingly, in some embodiments, the oxygenated fluid comprises at least 15 ppm oxygen at standard temperature and pressure, such as at least 20 ppm, 25 ppm, 30 ppm, 35 ppm, 40 ppm, 45 ppm, 50 ppm, 55 ppm, 60 ppm, 65 ppm, 70 ppm, 75 ppm, or 80 ppm oxygen, including ranges between any two of the listed values, for example 15 ppm-80 ppm, 20 ppm-80 ppm, 25 ppm-80 ppm, 30 ppm-80 ppm, 35 ppm-80 ppm, 40 ppm-80 ppm, 45 ppm-80 ppm, 50 ppm-80 ppm, 55 ppm-80 ppm, 60 ppm-80 ppm, 15 ppm-75 ppm, 20 ppm-75 ppm, 25 ppm-75 ppm, 30 ppm-75 ppm, 35 ppm-75 ppm, 40 ppm-75 ppm, 45 ppm-75 ppm, 50 ppm-75 ppm, 55 ppm-75 ppm, 60 ppm-75 ppm, 15 ppm-70 ppm, 20 ppm-70 ppm, 25 ppm-70 ppm, 30 ppm-70 ppm, 35 ppm-70 ppm, 40 ppm-70 ppm, 45 ppm-70 ppm, 50 ppm-70 ppm, 55 ppm-70 ppm, 60 ppm-70 ppm, 15 ppm-65 ppm, 20 ppm-65 ppm, 25 ppm-65 ppm, 30 ppm-65 ppm, 35 ppm-65 ppm, 40 ppm-65 ppm, 45 ppm-65 ppm, 50 ppm-65 ppm, 55 ppm-65 ppm, 60 ppm-65 ppm, 15 ppm-60 ppm, 20 ppm-60 ppm, 25 ppm-60 ppm, 30 ppm-60 ppm, 35 ppm-60 ppm, 40 ppm-60 ppm, 45 ppm-60 ppm, 50 ppm-60 ppm, or 55 ppm-60 ppm of dissolved oxygen. By way of example, the oxygenated fluid can comprise charge-stabilized oxygen-containing nanostructures. In some embodiments, the oxygenated fluid comprises, consists essentially of, or consists of a saline solution, for example saline for injection. It is contemplated that the oxygenated fluid can be sterile, for example suitable for (or formulated for) injection. In some embodiments, the oxygenated fluid does not comprise any cells or tissues of any organism. In some embodiments, the oxygenated fluid does not comprise blood. In some embodiments, the oxygenated fluid comprises, consists essentially of, or consists of a saline solution comprising at least 40 ppm oxygen. In some embodiments, the oxygenated fluid comprises charge-stabilized oxygen-containing nanostructures in an amount sufficient to provide modulation of at least one of cellular membrane potential and cellular membrane conductivity. In some embodiments, the oxygenated fluid is in an amount sufficient to protect hypoxic neurons from cell death. In some embodiments, the oxygenated fluid is in an amount sufficient to inhibit hypoxia in neurons of the subject. Accordingly, in the method of some embodiments, the administered oxygenated fluid is effective to protect hypoxic neurons from cell death. In some embodiments, the administered oxygenated fluid is effective to inhibit a decline in a behavior following the stroke, for example one or more of consciousness, defense reaction, grasp reflex, extremity movement, gait, circling, bradykinesia, balance, neglect, visual field cut/hemianopsia or facial weakness.

In some embodiments, the dissolved oxygen content, salinity, sterility, pH, etc., of the oxygenated fluid established at the time of electrokinetic production of the oxygenated fluid. As shown in Example 1, dissolved oxygen levels of oxygenated fluids (such as oxygenated fluids comprising charge-stabilized oxygen-containing nanostructures) of some embodiments herein can remain stable in a sealed container for many months. Accordingly, it is contemplated that a dissolved oxygen content of an oxygenated fluid, for example as a pharmaceutical product, at the time it was manufactured can be a suitable way of identifying the oxygenated fluid (as it may be impractical to determine a dissolved oxygen content at the exact time of clinical use). For example, the oxygenated fluid of methods (or corresponding uses or medicaments) some embodiments can have had a specified level of dissolved oxygen at the time it was manufactured, for example at least about 40 ppm dissolved oxygen. The amount of dissolved oxygen can refer to an amount at standard temperature and pressure, though this is simply in reference to a way of making a measurement, and in no way should be constructed to require that any or all of the manufacturing be performed at standard temperature and/or pressure. In some embodiments, the oxygenated fluid has a dissolved oxygen content (at standard temperature and pressure) of at least 15 ppm dissolved oxygen (at standard temperature and pressure, such as at least 20 ppm, 25 ppm, 30 ppm, 35 ppm, 40 ppm, 45 ppm, 50 ppm, 55 ppm, 60 ppm, 65 ppm, 70 ppm, 75 ppm, or 80 ppm, including ranges between any two of the listed values, for example, 20 ppm-80 ppm, 25 ppm-80 ppm, 30 ppm-80 ppm, 35 ppm-80 ppm, 40 ppm-80 ppm, 45 ppm-80 ppm, 50 ppm-80 ppm, 55 ppm-80 ppm, 60 ppm-80 ppm, 15 ppm-75 ppm, 20 ppm-75 ppm, 25 ppm-75 ppm, 30 ppm-75 ppm, 35 ppm-75 ppm, 40 ppm-75 ppm, 45 ppm-75 ppm, 50 ppm-75 ppm, 55 ppm-75 ppm, 60 ppm-75 ppm, 15 ppm-70 ppm, 20 ppm-70 ppm, 25 ppm-70 ppm, 30 ppm-70 ppm, 35 ppm-70 ppm, 40 ppm-70 ppm, 45 ppm-70 ppm, 50 ppm-70 ppm, 55 ppm-70 ppm, 60 ppm-70 ppm, 15 ppm-65 ppm, 20 ppm-65 ppm, 25 ppm-65 ppm, 30 ppm-65 ppm, 35 ppm-65 ppm, 40 ppm-65 ppm, 45 ppm-65 ppm, 50 ppm-65 ppm, 55 ppm-65 ppm, 60 ppm-65 ppm, 15 ppm-60 ppm, 20 ppm-60 ppm, 25 ppm-60 ppm, 30 ppm-60 ppm, 35 ppm-60 ppm, 40 ppm-60 ppm, 45 ppm-60 ppm, 50 ppm-60 ppm, or 55 ppm-60 ppm of dissolved oxygen at the time that the oxygenated fluid was manufactured. In some embodiments, the oxygenated fluid is a pharmaceutical saline solution that has one of the above-noted dissolved oxygen contents at the time that the oxygenated fluid was manufactured. In some embodiments, the oxygenated fluid is a saline solution comprising at least 40 ppm oxygen. In some embodiments, the oxygenated fluid is a saline solution comprising at least 50 ppm oxygen. In some embodiments, any of the oxygenated fluids described herein comprises charge-stabilized oxygen. In some embodiments, any of the oxygenated fluids described herein comprises charge-stabilized oxygen-containing nanostructures (such as nanobubbles). In some embodiments, the nanostructures of the oxygenated fluid comprise, consist essentially of, or consist of nanobubbles. As such, the oxygenated fluid can comprise stabilized oxygen-containing nanobubbles, a majority of the nanobubbles having a diameter of less than 100 nanometers.

Oxygenated fluids of methods, uses, and medicaments of some embodiments comprise modified or charged oxygen species. For example, the oxygenated fluid can comprise charge-stabilized oxygen-containing nanostructures. In some embodiments, the oxygen of the oxygenated fluid comprises, consists essentially of, or consists of molecular oxygen. In some embodiments, the oxygenated fluid is free of ozone, or comprises no more than trace amounts of ozone (e.g., amounts of ozone that have no observable physical or physiological effect). Without being limited by theory, it is contemplated that the oxygenated fluids (for example oxygenated fluids comprising charge-stabilized oxygen-containing nanostructures) of methods, uses, and medicaments of some embodiments comprises at least one of a form of solvated electrons, and electrokinetically modified or charged oxygen species. The electrokinetic modification can comprise, consist essentially of, or consist of oxygen-containing nanostructures stabilized by an imparted charge. In some embodiments, the oxygenated fluid comprises solvated electrons stabilized by molecular oxygen. In some embodiments, the solvated electrons or electrokinetically modified or charged oxygen species are present in the oxygenated fluid comprising charge-stabilized oxygen-containing nanostructures in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm.

It is noted that the oxygenated fluids in accordance with methods, uses, and medicaments of some embodiments have been shown to be stable in sealed containers for long periods of time (See, e.g., Example 1). In some embodiments, for the oxygenated fluid (for example, oxygenated fluid comprising charge-stabilized oxygen-containing nanostructures) of any of the methods, uses, or medicaments herein, oxygen in the oxygenated fluid has been present in an amount of at least 15 ppm at standard temperature and pressure for at least 3 hours. In some embodiments, for the oxygenated fluid of any of the methods, uses, or medicaments herein, oxygen in the oxygenated fluid comprising charge-stabilized oxygen-containing nanostructures has been present in an amount of at least 15 ppm at standard temperature and pressure for at least 1 month, such as at least 2, 3, 4, 5, or 6 months. In some embodiments, for the oxygenated fluid of any of the methods, uses, or medicaments herein, oxygen in the oxygenated fluid comprising charge-stabilized oxygen-containing nanostructures has been present in an amount of at least 40 ppm at standard temperature and pressure for at least 3 hours. In some embodiments, for the oxygenated fluid of any of the methods, uses, or medicaments herein, oxygen in the oxygenated fluid has been present in an amount of at least 40 ppm at standard temperature and pressure for at least 1 month, such as at least 2, 3, 4, 5, or 6 months. In some embodiments, the oxygenated fluid of any of the methods, uses, or medicaments herein comprises dissolved oxygen. In some embodiments, the oxygenated fluid of any of the methods, uses, or medicaments herein comprises charge-stabilized oxygen-containing nanostructures Oxygenated fluids (for example, oxygenated fluids comprising charge-stabilized oxygen-containing nanostructures) can be sterile and can be administered by an appropriate route. In some embodiments, at least one of the salinity, sterility, pH, etc., of the oxygenated fluid (e.g., an oxygenated fluid comprising charge-stabilized oxygen-containing nanostructures) is appropriately adjusted (e.g., using sterile saline or appropriate diluents) to be physiologically compatible with the route of administration prior to administration of the oxygenated fluid. Preferably, and diluents and/or saline solutions and/or buffer compositions used to adjust at least one of the salinity, sterility, pH, etc., of the fluids are also electrokinetic fluids, or are otherwise compatible. In some embodiments, the oxygenated fluid (for example, a fluid comprising charge-stabilized oxygen-containing nanostructures) is administered intravenously. In some embodiments, the oxygenated fluid is formulated for intravenous administration.

In some embodiments, the oxygenated fluid comprises saline (e.g., one or more dissolved salt(s); e.g., alkali metal based salts ($Li^+$, $Na^+$, $K^+$, $Rb^+$, $Cs^+$, etc.), alkaline earth based salts (e.g., $Mg^+$, $Ca^{++}$), etc., or transition metal-based positive ions (e.g., Cr, Fe, Co, Ni, Cu, Zn, etc.), in each case along with any suitable anion components, including, but not limited to $F^-$, $Cl^-$, $Br^-$, $I^-$, $PO4^-$, $SO4^-$, and nitrogen-based anions. Particular aspects comprise mixed salt based ionic solutions (e.g., $Na^+$, $K^+$, $Ca^{++}$, $Mg^{++}$, transition metal ion(s), etc.) in various combinations and concentrations, and optionally with mixtures of counterions. In some embodiments, the oxygenated fluid comprising charge-stabilized oxygen-containing nanostructures comprises standard saline (e.g., approx. 0.9% NaCl, or about 0.15 M NaCl). In particular aspects, the oxygenated fluid comprising charge-stabilized oxygen-containing nanostructures of methods, uses, and medicaments of some embodiments comprises saline at a concentration of at least 0.0002 M, at least 0.0003 M, at least 0.001 M, at least 0.005 M, at least 0.01 M, at least 0.015 M, at least 0.1 M, at least 0.15 M, or at least 0.2 M. In some embodiments, the conductivity of the oxygenated fluid is at least 10 µS/cm, at least 40 µS/cm, at least 80 µS/cm, at least 100 µS/cm, at least 150 µS/cm, at least 200 µS/cm, at least 300 µS/cm, or at least 500 µS/cm, at least 1 mS/cm, at least 5, mS/cm, 10 mS/cm, at least 40 mS/cm, at least 80 mS/cm, at least 100 mS/cm, at least 150 mS/cm, at least 200 mS/cm, at least 300 mS/cm, or at least 500 mS/cm. In some embodiments, any salt may be comprised by the oxygenated fluid. By way of example, any of the oxygenated fluids described herein may comprise charge-stabilized oxygen-containing nanostructures. In some embodiments, any salt may be comprised by the oxygenated fluid comprising charge-stabilized oxygen-containing nanostructures, provided that they allow for formation of biologically active salt-stabilized nanostructures (e.g., salt-stabilized oxygen-containing nanostructures) as disclosed herein.

Pharmaceutical Compositions, Medicaments, and Dosages

The oxygenated fluid of some embodiments (for example, an oxygenated fluid comprising charge-stabilized oxygen-containing nanostructures) can be part of a pharmaceutical composition, and/or for use as a medicament, and/or for medical use for treating, inhibiting, or ameliorating ischemic stroke or a symptom thereof. As such, in some embodiments, the oxygenated fluid is provided in a composition, such as a pharmaceutical composition, dosage form, or dosage unit in an amount effective for treating, inhibiting, or ameliorating ischemic stroke or a symptom thereof. In some embodiments, the amount of oxygenated fluid is effective to deliver oxygen of the oxygenated fluid to hypoxic brain cells of the subject upon intravenous administration of the oxygenated fluid. In some embodiments, the amount of oxygenated fluid is effective to deliver oxygen of the oxygenated fluid to brain cells that were subjected to ischemia followed by reperfusion upon intravenous administration of the oxygenated fluid comprising charge-stabilized oxygen-containing nanostructures. Examples of brain cells to which the oxygen can be delivered include glial cells (such as oligodendrocytes and/or microglia), or a combination of two or more of the listed cell types. In some embodiments, the administered oxygenated fluid is effective to inhibit a decline in a behavior following the stroke, for example one or more of consciousness, defense reaction, grasp reflex, extremity movement, gait, circling, bradykinesia, balance, neglect, visual field cut/hemianopsia or facial weakness. By way of example, if the oxygenated fluid comprises charge-stabilized oxygen-containing nanostructures, the delivered oxygen can be oxygen of charge-stabilized oxygen-containing nanostructures. In some embodiments, the amount of oxygenated fluid (for example, oxygenated fluid comprising charge-stabilized oxygen-containing nanostructures) in the pharmaceutical composition, dosage form, or dosage unit is at least about 2 cc/kg, for example at least about 2 cc/kg, 5 cc/kg, 10 cc/kg, 20 cc/kg, 25 cc/kg, 30 cc/kg, 40 cc/kg, 50 cc/kg, 70 cc/kg, 100 cc/kg, 200 cc/kg, or 500 cc/kg including ranges between any two of the listed values, for example, 2-10 cc/kg, 2-25 cc/kg, 2-50 cc/kg, 2-100 cc/kg, 2-500 cc/kg, 5-10 cc/kg, 5-25 cc/kg, 5-50 cc/kg, 5-100 cc/kg, 5-500 cc/kg, 10-25 cc/kg, 10-50 cc/kg, 10-100 cc/kg, 10-500 cc/kg, 20-50 cc/kg, 25-50 cc/kg, 20-100 cc/kg, 20-500 cc/kg, or 100-500 cc/kg (the amount of fluid in cc's can be determined based on the mass of the subject). In some embodiments, the amount of oxygenated fluid (for example, oxygenated fluid comprising charge-stabilized oxygen-containing nanostructures) in the pharmaceutical composition, dosage form, or dosage unit is at least about 100 cc, for example, at least about 100 cc, 150 cc, 500 cc, 1000 cc, 1500 cc, 2000 cc, 3000 cc, 4000 cc, or 5000 cc, including ranges between any two of the listed values, for example, 100-150 cc, 100-500 cc, 100-1000 cc, 100-1500 cc, 100-2000 cc, 100-2000 cc, 100-5000 cc, 150-500 cc, 150-1500 cc, 150-1500 cc, 150-2000 cc, 500-1000 cc, 100-2000 cc, 100-5000 cc, 500-1500 cc, 500-2000 cc, 500-5000 cc, 1000-1500 cc, 1000-2000 cc., or 1000-5000 cc. By way of example, the pharmaceutical composition as described herein may be formulated for intravenous administration.

In some embodiments, the oxygenated fluid is part of a pharmaceutical composition. As such, wherever a method, use, or medicament comprising the oxygenated fluid comprising charge-stabilized oxygen-containing nanostructures is mentioned herein, the corresponding method, use, or medicament comprising a pharmaceutical composition comprising, consisting essentially of, or consisting of the oxygenated fluid is also expressly contemplated. The pharmaceutical composition can comprise, consist essentially of, or consist of the oxygenated fluid. In some embodiments, the pharmaceutical composition comprises an active ingredient in addition to the oxygenated fluid. By way of example, for any of the pharmaceutical compositions described herein, the oxygenated fluid may comprise charge-stabilized oxygen-containing nanostructures.

In some embodiments, the oxygenated fluid (such as oxygenated fluid comprising charge-stabilized oxygen-containing nanostructures) is formulated for intravenous administration. As such, in some embodiments, the oxygenated fluid may be comprised by a pharmaceutical composition formulated for intravenous administration. Optionally, the pharmaceutical composition can include at least one additional active ingredient. In some embodiments, the pharmaceutical composition does not contain any active ingredients other than the oxygenated fluid. As such, the pharmaceutical composition can consist of, or consist essentially of the oxygenated fluid.

Methods of Treating, Inhibiting, or Ameliorating Ischemic Stroke

Some embodiments include a method of treating, inhibiting, or ameliorating ischemic stroke or a symptom thereof in a subject. It will be appreciated that treating, inhibiting, or ameliorating stroke or a symptom thereof, as used herein, can, in context, refer to treating, inhibiting, or ameliorating effects and damage resulting from stroke (for example, physiological damage such as infarct and/or behavioral effects, as described herein), depending on the timing of the method. For example, if an oxygenated solution is administered at or immediately after the onset of ischemic stroke, in context, it will be appreciated that while the stroke itself may no longer be prevented from occurring, damage and effects of the stroke may be treated, inhibited, or ameliorated. The method can comprise administering an oxygenated fluid as described herein to the subject, such as an oxygenated fluid comprising dissolved oxygen. The oxygenated fluid can be administered at or after the onset of ischemic stroke symptoms in the subject, for example by intravenous administration. For example, the oxygenated fluid can be administered to the subject at or immediately following the onset of the ischemic stroke symptoms, for example within 1, 3, 6, 12, 18, or 24 hours after the onset of the symptoms, including ranges between any two of the listed values, for example, 1-24 hours, 1-18 hours, 1-12 hours, 1-6 hours, 3-24 hours, 3-18 hours, 3-12 hours, 3-6 hours, 6-24 hours, 6-18 hours, 6-12 hours, 12-24 hours, 12-18 hours, or 18-24 hours. By way of example, the oxygenated fluid may comprise charge-stabilized oxygen-containing nanostructures. In some embodiments, the oxygenated fluid comprises, consists essentially of, or consists of a saline solution comprising at least 40 ppm oxygen. The oxygenated fluid can comprise at least 40 ppm oxygen at standard temperature and pressure. In some embodiments, the method comprises administering a dosage unit as described herein of the oxygenated fluid. In the method of some embodiments, the oxygenated fluid is administered as a first line treatment for ischemic stroke. In some embodiments, for any of the methods described herein, the oxygenated fluid comprises charge-stabilized oxygen-containing nanostructures. By way of example, the stroke can comprise acute ischemic stroke.

Figure 4A:
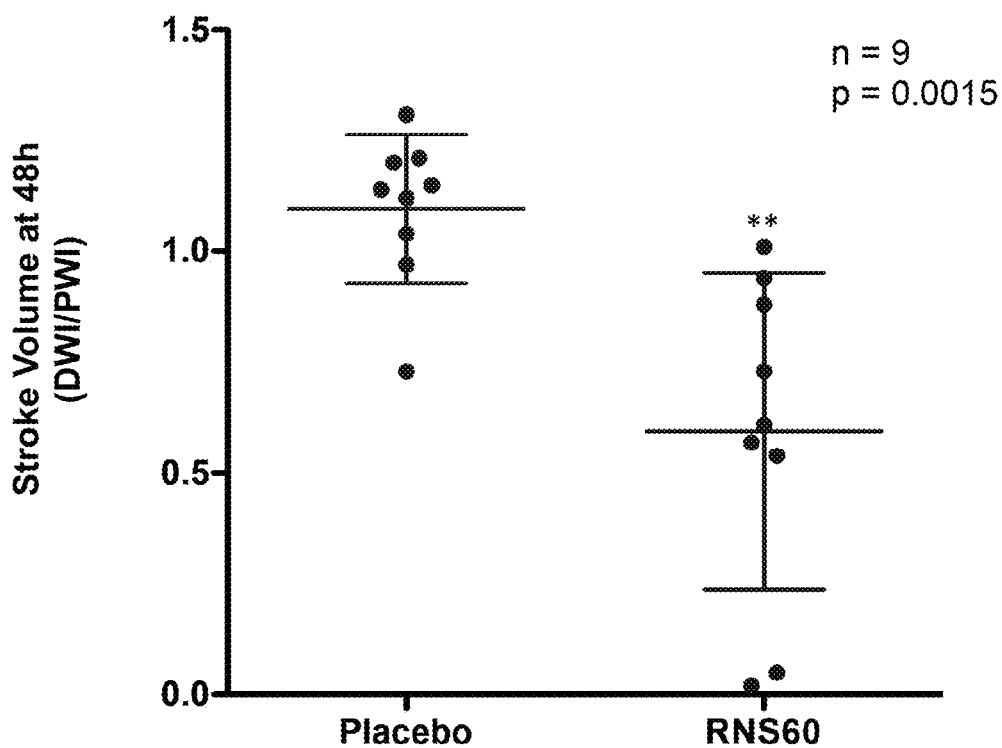
FIGS. 4A-C are a series of graphs showing effects of oxygenated fluids on a temporary (90 minute) middle cerebral artery occlusion (MCAO) model of stroke. Shown are effects on infarct volume (FIGS. 4A-B) and behavior (FIG. 4C).
Figure 4B:
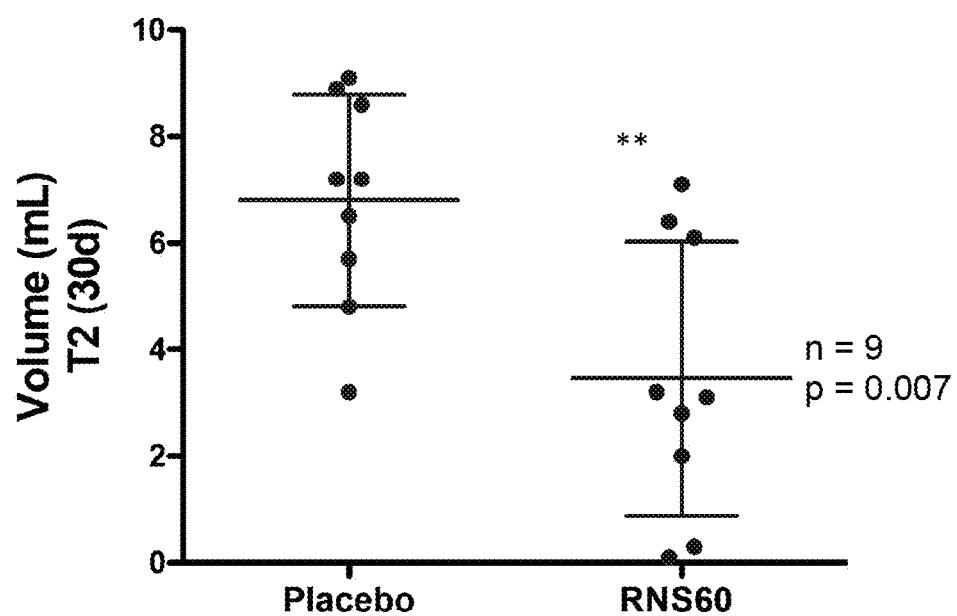
Figure 4C:
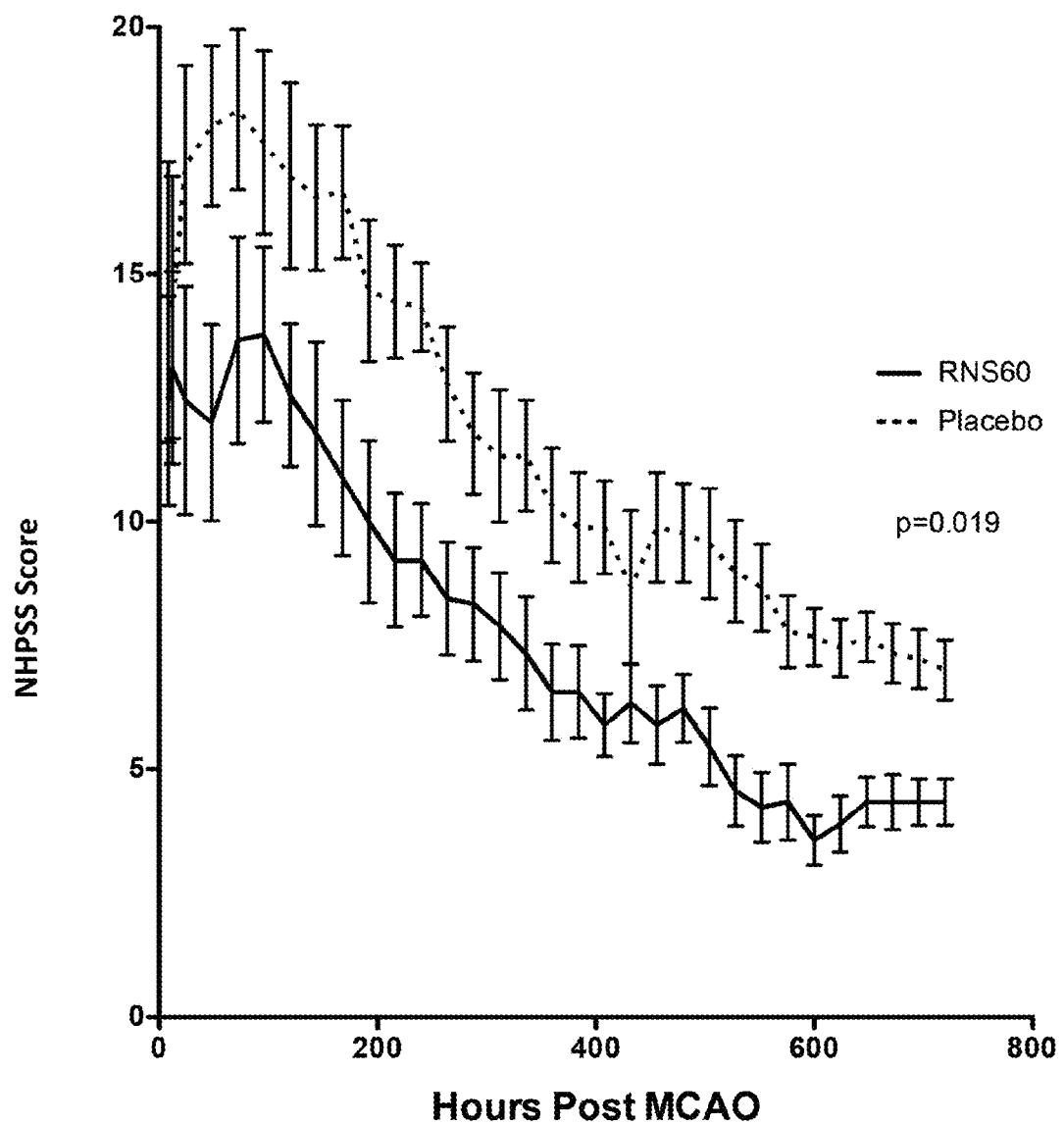

It has been observed herein that administering an oxygenated fluid (such as an oxygenated fluid comprising charge-stabilized oxygen-containing nanostructures) within 5 minutes or 60 minutes of occlusion in a primate model of ischemic stroke significantly reduces brain lesion size compared to saline-treated controls (Example 2 and FIGS. 2A-B; and Example 4 and FIGS. 4A-C). Accordingly, it is contemplated that the oxygenated fluid of some embodiments can have neuroprotective effects (without being limited by theory, it is contemplated that the oxygenated fluid can provide oxygen to hypoxic brain cells in the subject and/or brain cells that were subjected to ischemia followed by reperfusion, such as neurons and/or glial cells as described herein). In some embodiments, the oxygenated fluid can be administered at the time of, or immediately following the onset of stroke symptoms, for example within 1, 2, 3, 4, 5, 6, 12, 18, or 24 hours after the onset of stroke symptoms, including ranges between any two of the listed values, for example, within 1-24 hours, 1-18 hours, 1-12 hours, 1-6 hours 1-3 hours, 2-24 hours, 2-18 hours, 2-12 hours, 2-6 hours, 3-24 hours, 3-18 hours, 3-12 hours, 3-6 hours, 6-24 hours, 6-18 hours, 6-12 hours, 12-24 hours, 12-18 hours, 18-24 hours, 2-6 hours, 4-6 hours, 5-6 hours, 1-5 hours, 2-5 hours, 3-5 hours, 4-5 hours, 1-4 hours, 2-4 hours, 3-4 hours, 1-3 hours, or 2-3 hours, of the onset of stroke symptoms. In the method of some embodiments, administering the oxygenated fluid comprises delivering oxygen of the oxygenated fluid to hypoxic brain cells of the subject. Examples of brain cells to which the oxygenated fluid can be delivered include neurons, glial cells (such as oligodendrocytes and/or microglia), or a combination of two or more of the listed cell types. For example, if the oxygenated fluid comprises charge-stabilized oxygen-containing nanostructures, the delivered oxygen may be of charge-stabilized oxygen-containing nanostructures. In some embodiments, administering the oxygenated fluid comprises delivering oxygen to brain cells that were subjected to ischemia followed by reperfusion (such as neurons and/or glial cells as described herein). The oxygenated fluid is not necessarily administered directly to the brain cells, and can be delivered indirectly (for example via intravenous injection). In some embodiments, the oxygenated fluid is not administered by inhalation. In some embodiments, the oxygenated fluid is not administered hyperbarically, and/or the oxygenated fluid is not administered normobarically. In some embodiments, the administered fluid is effective to inhibit or prevent hypoxia of brain cells of the subject. Examples of brain cells in which hypoxia can be prevented include neurons, glial cells (such as oligodendrocytes and/or microglia), or a combination of two or more of the listed cell types. In some embodiments, the administered oxygenated fluid is effective to prevent reperfusion damage to brain cells that were subjected to ischemia followed by reperfusion, for example neurons and/or glial cells as described herein. In some embodiments, the administered oxygenated fluid is effective to prevent death of brain cells that were subjected to ischemia followed by reperfusion, for example neurons and/or glial cells as described herein. In some embodiments, the administered oxygenated fluid is administered in an amount effective to prevent reperfusion damage to brain cells that were subjected to ischemia followed by reperfusion, for example neurons and/or glial cells as described herein. In some embodiments, the administered oxygenated fluid is administered in an amount effective to prevent death of brain cells that were subjected to ischemia followed by reperfusion, for example neurons and/or glial cells as described herein. In some embodiments, the administered oxygenated fluid is administered in an amount effective to inhibit or prevent hypoxia of brain cells of the subject. Examples of brain cells in which hypoxia can be prevented include neurons, glial cells (such as oligodendrocytes and/or microglia), or a combination of two or more of the listed cell types. In some embodiments, the administered oxygenated fluid is administered in an amount effective to inhibit a decline in a behavior following the stroke, for example one or more of consciousness, defense reaction, grasp reflex, extremity movement, gait, circling, bradykinesia, balance, neglect, visual field cut/hemianopsia or facial weakness. In some embodiments, for any methods described herein, the oxygenated fluid comprises charge-stabilized oxygen-containing nanostructures.

Symptoms indicative of the onset of an ischemic stroke are well-known in the art. Example symptoms include paralysis or numbness or droopiness of the face, arm or leg; speech that is slurred or difficult to understand; blurred or blackened vision in one or both eyes; headache; dizziness; and difficulty maintaining balance. In some embodiments, the oxygenated fluid is administered to the subject prior to any acute inflammatory response to the ischemic stroke. In some embodiments, the method comprises identifying the subject as suffering from, or likely to be suffering from an ischemic stroke prior to administering the oxygenated fluid. In some embodiments, the subject is a human.

In the method of some embodiments, administering the oxygenated fluid inhibits, ameliorates, treats, or prevents at least one symptom of stroke. The symptom can be a symptom of long-term stroke-induced damage, for example, numbness, weakness, or stiffness, impaired speech production and/or comprehension, impaired cognition, and/or mood dysregulation, or two or more of the listed items. In some embodiments, the oxygenated fluid (for example, oxygenated fluid comprising charge-stabilized oxygen-containing nanostructures) has neuroprotective effects in a subject in need thereof, for example a subject suffering from stroke. For example, in some embodiments, the oxygenated fluid is effective in enhancing, increasing, or supporting non-inflammatory microglia, increase in survival, maturation and function of oligodendrocytes, augmentation of neuronal branching, plasticity and neurotransmission, enhancement of neuronal survival (anti-apoptotic), stimulation of mitochondrial biogenesis and function, or a combination of two or more of the listed items. In some embodiments, administering the oxygenated fluid inhibits a decline in at least one behavior following the stroke, for example a decline in consciousness, defense reaction, grasp reflex, extremity movement, gait, circling, bradykinesia, balance, neglect, visual field cut/hemianopsia or facial weakness, or a combination of two or more of any of the listed items. It will be appreciated that following a stroke, in the absence of treatment as described herein, one or more of the listed behaviors may decline. An inhibition of the decline may be observed, for example, as a lack or prevention of decline, or as a lesser degree of decline than would be expected in the absence of the treatment as described herein.

In the method of some embodiments, the oxygenated fluid (for example, oxygenated fluid comprising charge-stabilized oxygen-containing nanostructures) is administered to the subject at a rate of at least about 0.1 cc/kg/h, for example at least about 0.1, 0.5, 1, 2, 4, 5, 7, 10, 20, 25, or 30 cc/kg/h, including ranges between any two of the listed values, for example, about 0.1-2 cc/kg/h, 0.1-4 cc/kg/h, 0.1-5 cc/kg/h, 0.1-7 cc/kg/h, 0.1-10 cc/kg/h, 0.1-20 cc/kg/h, 0.1-30 cc/kg/h, 0.5-2 cc/kg/h, 0.5-4 cc/kg/h, 0.5-5 cc/kg/h, 0.5-7 cc/kg/h, 0.5-10 cc/kg/h, 0.5-20 cc/kg/h, 0.5-30 cc/kg/h, 1-4 cc/kg/h, 1-5 cc/kg/h, 1-7 cc/kg/h, 1-10 cc/kg/h, 1-20 cc/kg/h, 1-30 cc/kg/h, 2-4 cc/kg/h, 2-5 cc/kg/h, 2-7 cc/kg/h, 2-10 cc/kg/h, 2-20 cc/kg/h, 2-30 cc/kg/h, 5-7 cc/kg/h, 5-10 cc/kg/h, 5-20 cc/kg/h, 5-30 cc/kg/h, 10-20 cc/kg/h, or 10-30 cc/kg/h. In some embodiments, the administration occurs for at least 1, 2, 3, 4, 5, 6, or 10 hours after the stroke, including ranges between any two of the listed values. As such, in some embodiments, at least about 0.1 cc/kg of oxygenated fluid, for example at least about 0.1, cc/kg, 0.5 cc/kg, 1 cc/kg, 2 cc/kg, 5 cc/kg, 10 cc/kg, 20 cc/kg, 25 cc/kg, 50 cc/kg, 70 cc/kg, 100 cc/kg, or 200 cc/kg, including ranges between any two of the listed values, are administered to the subject. In the method of some embodiments, the oxygenated fluid is administered continuously. In the method of some embodiments, the oxygenated fluid is administered continuously in two or more discrete events, separated by time periods of non-administration. In some embodiments, the rate of administration of the oxygenated fluid is constant over the time period of administration. In some embodiments, the rate of administration of the oxygenated fluid varies over the time period of administration. In some embodiments the oxygenated fluid can be administered at a first rate for a first time period, and administered at a lower rate for a second, subsequent time period. For example, the oxygenated fluid can first be administered at a first rate of about 5-10 cc/kg/h for at least about an hour, and then administered at a second rate of about 0.5-4 cc/kg/h for at least 5, 7, 9, or 10 hours. For example, the oxygenated fluid can first be administered at a first rate of about 5-10 cc/kg/h for at about 1-2 hours, and then administered at a lower a second rate of about 0.5-4 cc/kg/h for at least 5, 7, 9, or 10 hours. In some embodiments, for any method described herein, the oxygenated fluid comprises charge-stabilized oxygen-containing nanostructures.

In the method of some embodiments, the oxygenated fluid comprises saline. In the method of some embodiments, the oxygen in the oxygenated fluid comprises modified or charged oxygen species. In the method of some embodiments, the oxygenated fluid comprises no more than trace amounts of ozone. In the method of some embodiments, the oxygen in the oxygenated fluid has been present in an amount of at least 15 ppm at standard temperature and pressure for at least 3 hours. In the method of some embodiments, the oxygen in the oxygenated fluid has been present in an amount of at least 40 ppm at standard temperature and pressure for at least 3 hours. In some embodiments, for any method described herein, the oxygenated fluid comprises charge-stabilized oxygen-containing nanostructures. In the method of some embodiments, the nanostructures comprise nanobubbles, a majority of the nanobubbles having a diameter of less than 100 nanometers.

In the method of some embodiments, the method further comprises administering an additional therapeutic agent to the subject, for example tissue plasminogen activator such as intravenous alteplase. In some embodiments, the method further comprises performing a thrombectomy and/or embolectomy on the subject.

Example 1: Stability of Fluids Comprising Charge-Stabilized Oxygen-Containing Nanostructures Fluid comprising charge-stabilized oxygen-containing nanostructures was generated using a Mixing Device as described in U.S. Pat. No. 9,745,567. The solution was used to manufacture drug product, a solution that contains charge-stabilized oxygen gas-containing nanostructures having an average diameter of less than 100 nanometers.

For this example lot of drug product, bulk drug substance was manufactured in bulk, then filled into drug product containers, and drug product was prepared. At the time that the drug product of this Example was prepared, (e.g., filled in syringes, IV bags, or glass vials) its dissolved oxygen content was spec'd at greater than or equal to 50 ppm.

Figure 1:
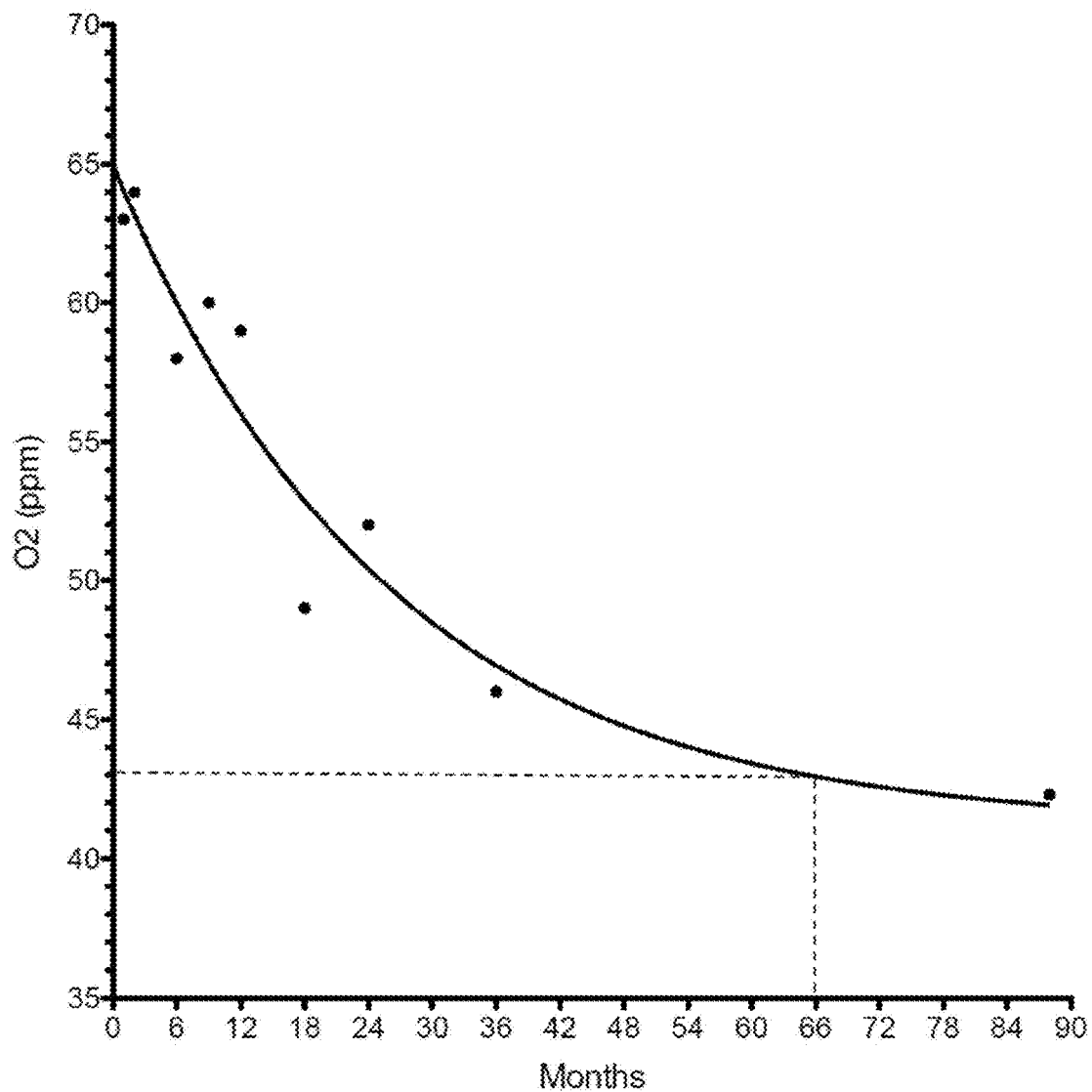
FIG. 1 is a graph illustrating an example curve of dissolved oxygen stability for an oxygenated fluid over time. The oxygenated fluid for FIG. 1 is RNS60. Without being limited by theory RNS60 is contemplated to comprise charge-stabilized oxygen-containing nano structures.

Lot release testing was done for this example lot of drug product. Extended testing of oxygen levels was performed to establish a DO profile over time. FIG. 1 shows a curve obtained for lot stability over time. At 66 months after filling, this lot had a DO content of about 43 ppm.

At 66 months, the oxygenated fluid comprising charge-stabilized oxygen-containing nanostructures from this lot was collected and tested for anti-inflammatory activity in a mouse model of inflammation. Female SJL/j mice were immunized with MBP and on day 10 of immunization, spleens and lymph nodes were harvested, followed by treatment of splenocytes and lymph node cells in the presence of 5% and 10% drug product (fluid comprising charge-stabilized oxygen-containing nanostructures) from the lot (66 months after filling) or one of its controls or processing variants. After 24 hours, mRNA expression of Foxp3 and IL-10 as well as other related markers of Treg, Th17, Th1 and Th2 were measured as reported in an earlier study (Mondal et al., PLoS One 7: e 51869 2012). Drug product from the lot (comprising fluid comprising charge-stabilized oxygen-containing nanostructures), with a DO level as low as 43 ppm, showed the activities of reversing MBP-induced reduction in IL-10 and the Treg marker FoxP3.

Thus, it has been shown that fluid comprising charge-stabilized oxygen-containing nanostructures comprising saline and having at least 50 ppm dissolved oxygen at the time of manufacture (in accordance with methods, uses, and medicaments of some embodiments herein) can be successfully produced, and can stably maintain dissolved oxygen levels for at least 66 months. Moreover, after 66 months, the oxygenated fluid comprising charge-stabilized oxygen-containing nanostructures retained activity in vivo.

Example 2: Treatment of Non-Human Primate Middle Cerebral Artery Occlusion by Intravenous Administration of Oxygenated Fluid Animal Handling, Housing and Pre-Operative Care Ten male captive bred cynomolgus macaques (4.5-5.5 kg) were pair housed in an environmentally controlled and enclosed primate colony of 10-40 animals on a 12 h light dark cycle (light on 0600 h to 1800 h). Caging consisted of 115×115×200 cm home cages with adjoining recreation cages accessible during the light hours. The colony was supervised daily by a team consisting of the principal investigator, a veterinarian, two veterinary technicians with non-human primate training and experience. Animals were provided with water ad lib, daily complete diet in the form of monkey chow (Purina Canada, Mississauga, ON) and mixed dietary enrichment in the form of nuts, fresh fruit and vegetables throughout the day. Environmental enrichment in the form of puzzles, primate specific toys and audiovisual media were provided during light hours. Prior to administration of anesthesia animals were fasted for 12 hours.

In this protocol anesthesia was required for both surgical procedures and imaging. Fasted animals were sedated in their home cage using Medetomidine (0.15 mg/kg, intramuscular). When sedative effect was attained the animals were hand caught by a veterinarian or technician with assistance from a second technician controlling the primate collar on pole. Animals were carried to an induction room where isoflurane is applied at 5% in 95% Oxygen at a rate of 2 L/min by facemask until the animal is adequately anesthetized for intubation. Endotracheal intubation with a cuffed 2.5-3.0 Fr endotracheal tube was achieved under direct laryngoscopy. A peripheral 21G intravenous catheter was placed in the saphenous vein and lactated Ringer's solution was administered at a maintenance rate (0.5 mL/kg/hr). Eyes were lubricated with Tear-Gel. Surgical areas specific to the procedure to be undertaken, including groin, axilla, back (for monopolar ground pad) and scalp, were shaved and cleansed with alcohol solution. Non-invasive monitoring including blood pressure by leg cuff, end-tidal $CO_2$, oxygen saturation, electrocardiogram and temperature by rectal probe were recorded and corrected to maintain values within physiologic norms. The animal was transported to the operating room thereafter.

Surgical Procedure

The animal was placed on the operating table in supine position and the head was pinned in a custom head rest. The head was positioned in extension and left lateral rotation so the right pterion was superior in orientation. Airway patency was ensured and physiologic monitoring equipment was placed prior to covering the torso with a heated air blanket. Anesthesia depth and physiologic stability were monitored and adjusted by a veterinarian. The right scalp was scrubbed with iodine prep solution and draped in an aseptic fashion. Prior to skin incision prophylactic Cefazolin (20 mg/kg IV) was administered.

The middle cerebral artery (MCA) was prepared distal to lenticulostriates just proximal to the orbitofrontal branch for aneurysm clip placement. A 5 mm Sundt clip was placed on the vessel. Inspection of the vessel under the microscope confirmed complete occlusion.

Following vessel occlusion (MCAO) the craniotomy was irrigated with warm 0.9% NaCl solution and the dura was closed with 6-0 silk suture. The temporalis muscle and fascia were closed with 3-0 vicryl suture. The skin was closed in two layers with 4-0 vicryl suture. The incision was cleansed and covered with Neosporin ointment. The animal was transferred under anesthetic to the MRI scanner.

Dosing and Blinding

Study drug consisted of intravenous RNS60 (a saline fluid comprising charge-stabilized oxygen-containing nanostructures, spec'd at greater than or equal to 50 ppm dissolved oxygen) versus Placebo solution (normal saline). Study drug was provided in 375 mL intravenous bags (one IV bag per animal). Each bag had a unique code, held by Revalesio Corporation, to blind investigators from drug identity. Intravenous fluids were stored at 4° C. until use. IV bags were hung at room temperature, but not punctured, 1 hour before anticipated infusion start. Five minutes after MCAO the Ringer's Lactate maintenance infusion was stopped and the RNS60/Placebo infusion initiated. The intravenous bag was punctured as per manufacturer's instructions and the line was flushed and attached to the intravenous catheter. Intravenous infusion of the oxygenated fluid commenced at 5 cc/kg/h, 5 minutes after MCAO onset. After 1 hour the infusion was reduced to 2.5 cc/kg/h until the time of transcardial perfusion/sacrifice.

Serial Imaging

Immediately after surgery animals were transported to the MRI. MRI scanning consisted of an initial DWI scan to quantify infarction at baseline. This was immediately followed by a perfusion scan to define the region of ischemia/tissue at risk for infarction. This established the ischemic penumbra volume (Penumbra=DWI-PWI) at baseline. DWI scans were obtained serially at 0.5, 1, 2, 3, 5 and 6 hours. Once every 3 hours a perfusion scan was obtained to assess any changes in perfusion. The second-to-last scan obtained was a T2 weighted MRI to assess for parenchymal edema.

Imaging was performed on a 3T Siemens TRIO system using a 32 channel head coil. Animals were placed in prone position in a custom made acrylic cylindrical sled with the neck extended. The animal was fixed in place using tape and wrapped in a heated water blanket. The animal and sled were placed in the center of the radiofrequency volume coil and positioned within the magnet bore. Long ventilator/gas supply tubing, intravenous and arterial lines were run to the control room to associated machinery. Physiological monitoring was maintained throughout using MRI compatible ECG, respiratory and temperature monitors.

Results

Results of the study are shown in FIGS. 2A and 2B. DWI volume (FIG. 2A), and DWI as a percentage of PWI (FIG. 2B) were measured by MRI at 0.5, 1, 2, 3, 4, 5, and 6 hours after induction of the occlusion (which was followed 5 minutes later by administration of RNS60 or normal saline). At each of these timepoints, total lesion volume (DWI volume), as well as DWI as a percentage of PWI were significantly decreased in the primates treated with RNS60 compared to normal saline controls. Thus, it has been shown that fluid comprising charge-stabilized oxygen-containing nanostructures in accordance with some embodiments is effective at treating, reducing, or ameliorating stroke in vivo.

As shown herein, consistent with neuroprotective effects of RNS60, intravenous injection of RNS60 has been observed to impact cellular processes in the brain. Khasnavis et al. observed that following intraperitoneal injection in a mouse model of Parkinson's disease, RNS60 induced significant activation of type IA PI3 Kinase at the cell membrane of the substantia nigra (See Khasnavis et al. J. Neuroimmune Pharmacol (2014) 9: 218-32, hereby incorporated by reference in its entirety, at p. 226 and FIG. 3). Additionally, Modi et al. observed that intraperitoneal injection of RNS60 inhibited activation of iNOS in the hippocampus (Modi et al., PLoS One (2014) 9: e103606, hereby incorporated by reference in its entirety, at p. 10 and FIG. 8). Taken together, (i) the ability of injected fluids comprising charge-stabilized oxygen-containing nanostructures to modulate cellular processes in the brain, and (ii) their further ability to inhibit brain lesions in stroke, are consistent with these fluids having neuroprotective effects. Without being limited by theory, it is contemplated that fluids comprising charge-stabilized oxygen-containing nano structures can provide oxygen to hypoxic brain cells and/or brain cells that were subjected to ischemia followed by reperfusion. Examples of brain cells include neurons and/or glial cells (e.g., oligodendrocytes and/or microglia).

Example 3: Treatment of Rat Model of Stroke with Oxygenated Fluid

Figure 3:
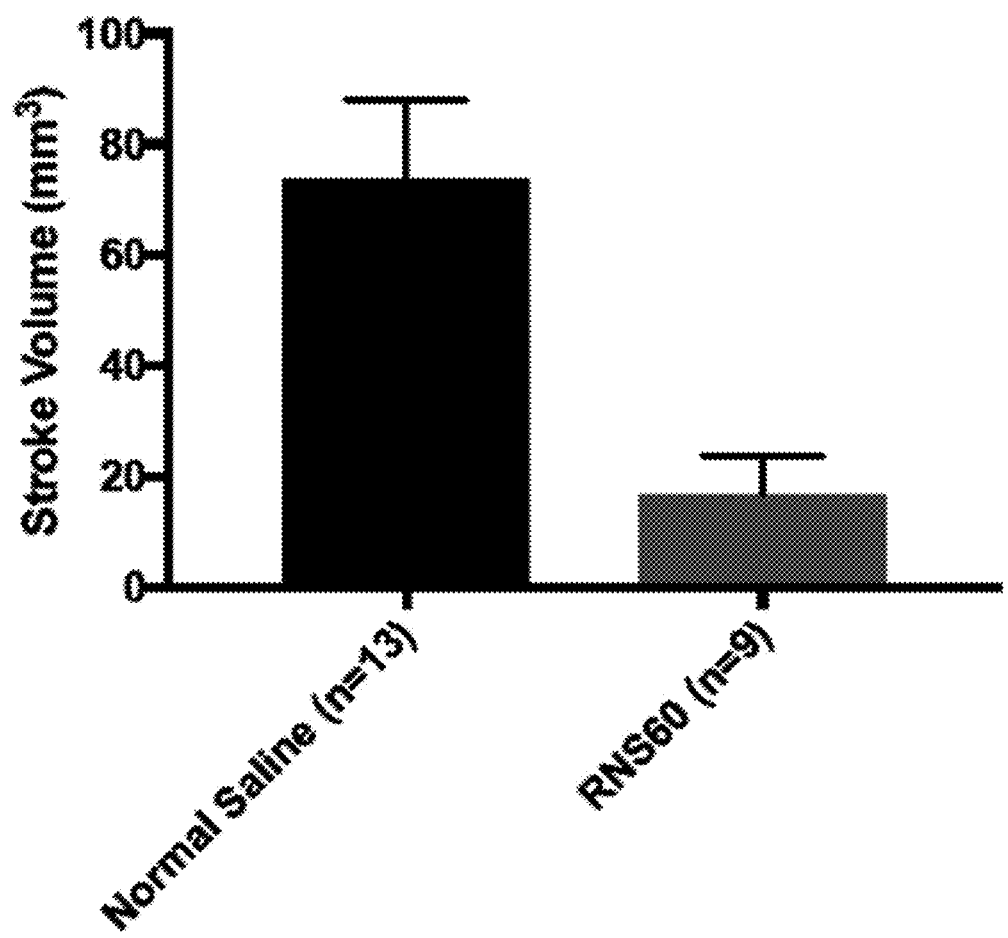
FIG. 3 is a graph showing 24 h stroke volume in a rat model of ischemic stroke for rats treated with an oxygenated fluid according to some embodiments ("RNS60"), and for normal saline-treated controls.

An oxygenated fluid according to some embodiments ("RNS60," which comprises charge-stabilized oxygen-containing nanostructures) was tested using a recovery model of MCAO in rats. Briefly, rats were anaesthetized and subjected to 120 minute MCAO (retrograde filament plus CCA Occlusion). Drug infusion was initiated (v/w 5% body weight @ 1 mL per 2 minutes) 5 minutes following occlusion. Normal saline was administered to control animals. Animals were recovered under a heat lamp. Neurological examinations were undertaken to identify circling patterns and hemiparesis confirming brain ischemia. After 24 hours, animals were sacrificed and brain tissue was harvested for TTC Staining. The results are shown in FIG. 3. The results indicate that stroke volume was significantly lower in the brains of rats that received the oxygenated fluid comprising charge-stabilized oxygen-containing nanostructures, compared to saline-treated controls.

Example 4: Non-Human Primate Model of Acute Ischemic Stroke

In the following example, a cynomolgus macaque transient (90 minute) MCAO occlusion model was used, oxygenated solution was administered 60 minutes after MCAO, and behavioral effects were subsequently monitored. Eleven male cynomolgus macaques/group were subjected to temporary (90 min) MCAO. Animal care and surgical procedures were as in Example 2, except that the MCA was subject to temporary (90 minutes) occlusion by a 5 mm Sundt clip placed on the MCA so as to model transient stroke.

Study drug was intravenous RNS60 (an oxygenated saline spec'd at greater than or equal to 50 ppm dissolved oxygen) versus Placebo solution (normal saline). Study drug was provided in 375 mL intravenous bags (one IV bag per animal). Each bag had a unique code to blind investigators from drug identity.

Intravenous infusion of the fluid (RNS60 or normal saline Placebo) commenced at 5 cc/kg/h, 60 minutes after MCAO. After 1 hour, the infusion was reduced to 2.5 cc/kg/h for 48 hours. MRI scans were obtained at 48 hours. The stroke volumes measured by the MRI imaging at 48 hours are shown in FIG. 4A. The RNS60 treatment group had a significantly lower infarct volume than the normal saline treatment group (n=9; p=0.0015).

Animals were then followed-up for 30 days with behavioral tests (Non-human Primate Stroke Scale, NHPSS). The NHPSS scores for 30 days are shown in FIG. 4C. The NHPSS scores were consistently superior in the RNS60 treatment group compared to the normal saline controls.

MRI (T2) scans were performed at 30 days. The results of the 30-day MRI scans are shown in FIG. 4B. Consistent with the 48-hour results, the RNS60 treatment group had a significantly lower infarct volume at 30 days than the normal saline treatment group (n=9; p=0.007).

This example shows that in a primate model of acute ischemic stroke (90 min temporary occlusion), intravenously administering an oxygenated solution (RNS60) one hour after occlusion in accordance with some embodiments herein yielded neuroprotective effects, as indicated by reduced infarct volume (48 hours after treatment) and improved NHPSS scores (30 days post occlusion) compared to controls.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods, compositions, kits, and uses described herein without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method is disclosed herein, for example a method of inhibiting, treating, or ameliorating the symptoms of stroke in a subject is disclosed herein, the corresponding use, or composition or medicament for use is also expressly contemplated. For example, for the disclosure of "a method of inhibiting, treating, or ameliorating the symptoms of stroke comprising administering an oxygenated fluid" (e.g., an oxygenated fluid comprising charge-stabilized oxygen-containing nanostructures) also contemplated is an oxygenated fluid (e.g., an oxygenated fluid comprising charge-stabilized oxygen-containing nanostructures) for use in of inhibiting, treating, or ameliorating the symptoms of stroke.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A method of treating, inhibiting, or ameliorating ischemic stroke or a symptom thereof in a subject, the method comprising:
    identifying the subject as suffering from, or likely to be suffering from an ischemic stroke or a symptom thereof, and
    administering an oxygenated fluid comprising charge stabilized oxygen-containing nanostructures to the subject intravenously at a rate of about 1 to 2 cc/kg/hr for a duration of at least 10 hours.

2. The method of claim 1, wherein the oxygenated fluid is a pharmaceutical saline solution comprising charge-stabilized oxygen-containing nanostructures, a majority of the nanostructures having a diameter of less than 100 nanometers, wherein the pharmaceutical saline solution comprised at least 20 ppm oxygen at the time it was manufactured.

3. The method of claim 2, wherein the nanostructures comprise nanobubbles, a majority of the nanobubbles having a diameter of less than 100 nanometers.

4. The method of claim 1, wherein the oxygenated fluid is administered for at least 48 hours.

5. The method of claim 1, wherein the oxygenated fluid is administered in two or more discrete events, separated by time periods of non-administration.

6. The method of claim 1, wherein the oxygenated fluid comprises at least 40 ppm oxygen at standard temperature and pressure.

7. The method of claim 1, wherein the oxygenated fluid comprises saline.

8. The method of claim 1, wherein the oxygenated fluid does not comprise blood or perfluorocarbon.

9. The method of claim 1, wherein the oxygenated fluid is oxygenated by dissolved oxygen.

10. The method of claim 1, wherein at least 50% of the oxygenation in the oxygenated fluid comprises dissolved oxygen.

11. The method of claim 1, wherein the oxygen in the oxygenated fluid has been present in an amount of at least 15 ppm at standard temperature and pressure for at least 3 hours.

12. The method of claim 1, wherein the oxygen in the oxygenated fluid comprises modified or charged oxygen species.

13. The method of claim 1, wherein the oxygenated fluid comprises no more than trace amounts of ozone.

14. The method of claim 1, further comprising administering an additional therapeutic agent to the subject.

15. The method of claim 1, wherein said administering comprises delivering the oxygen of the oxygenated fluid to brain cells of the subject, wherein said brain cells were subjected to ischemia followed by reperfusion.

16. The method of claim 1, wherein the administered oxygenated fluid is effective to inhibit hypoxia of brain cells, inhibit reperfusion damage to brain cells, or inhibit a decline in a behavior following the ischemic stroke, or any combination thereof, of the subject.

17. The method of claim 16, wherein the behavior is selected from the group consisting of: consciousness, defense reaction, grasp reflex, extremity movement, gait, circling, bradykinesia, balance, neglect, visual field cut/hemianopsia or facial weakness, or a combination of two or more of any of the listed items.

* * * * *

UNITED STATES PATENT AND TRADEMARK OFFICE
CERTIFICATE OF CORRECTION

PATENT NO. : 12,263,188 B2
APPLICATION NO. : 17/187437
DATED : April 1, 2025
INVENTOR(S) : Supurna Ghosh et al.

It is certified that error appears in the above-identified patent and that said Letters Patent is hereby corrected as shown below:

On the Title Page

In item (56) Other Publications, Column 2, Line 1, delete "ALS" Webmed, 2019," and insert -- ALS" WebMD, 2019, --.

In item (56) Other Publications, Column 1, Line 14, delete "Ella et al.," and insert -- Elia et al., --.

In item (56) Other Publications, Column 2, Line 26, delete "protective glla and" and insert -- protective glia and --.

In item (56) Other Publications, Column 2, Line 31, delete "Opinion malled Nov." and insert -- Opinion mailed Nov. --.

In item (56) Other Publications, Column 2, Line 47, delete "Announces Positivetopline Data" and insert -- Announces Positive Topline Data --.

In item (56) Other Publications, Column 2, Line 48, delete "RNS60 Inpatients With" and insert -- RNS60 In Patients With --.

In item (56) Other Publications, Column 2, Line 49, delete "Acute Ischemicstroke in" and insert -- Acute Ischemic Stroke in --.

In the Specification

Column 3, Line 16, delete "oxygen-containing nano structures." and insert -- oxygen-containing nanostructures. --.

Column 5, Line 5, delete "containing nano structures are" and insert -- containing nanostructures are --.

Signed and Sealed this
Twentieth Day of May, 2025

Coke Morgan Stewart
*Acting Director of the United States Patent and Trademark Office*

CERTIFICATE OF CORRECTION (continued)
U.S. Pat. No. 12,263,188 B2

Column 8, Line 49, delete "oxygen-containing nanostructures" and insert -- oxygen-containing nanostructures. --.

Column 9, Line 4, delete (e.g., $Mg^+$, $Ca^{++}$)," and insert -- (e.g., $Mg^{++}$, $Ca^{++}$), --.

Column 9, Line 7, delete "$I^-$, $PO4^-$, $SO4^-$, and" and insert -- $I^-$, $PO_4^-$, $SO_4^-$, and --.

Column 17, Lines 12-13, delete "containing nano structures can" and insert -- containing nanostructures can --.

In the Claims

In Claim 1, Column 20, Line 7, delete "symptom thereof, and" and insert -- symptom thereof; and --.